(12) United States Patent
Brüschweiler et al.

(10) Patent No.: US 9,594,880 B2
(45) Date of Patent: Mar. 14, 2017

(54) METHODS FOR QUANTITATIVE ANALYSIS OF METABOLIC MIXTURES BY 2D $^{13}$C-CONSTANT-TIME TOCSY NMR SPECTROSCOPY

(71) Applicant: FLORIDA STATE UNIVERSITY RESEARCH FOUNDATION, INC., Tallahassee, FL (US)

(72) Inventors: Rafael Brüschweiler, Tallahassee, FL (US); Kerem Bingol, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 434 days.

(21) Appl. No.: 14/278,003

(22) Filed: May 15, 2014

(65) Prior Publication Data

US 2014/0343873 A1  Nov. 20, 2014

Related U.S. Application Data

(60) Provisional application No. 61/823,560, filed on May 15, 2013.

(51) Int. Cl.
| | |
|---|---|
| *G06F 11/00* | (2006.01) |
| *G06F 19/00* | (2011.01) |
| *G01N 24/08* | (2006.01) |
| *G01R 33/46* | (2006.01) |

(52) U.S. Cl.
CPC ........... *G06F 19/703* (2013.01); *G01N 24/08* (2013.01); *G01R 33/4633* (2013.01)

(58) Field of Classification Search
CPC ... G01R 33/465; G01R 33/4625; G01N 24/08

USPC .................................... 702/28, 30, 182–185
See application file for complete search history.

(56) References Cited

U.S. PATENT DOCUMENTS 8,380,445 B2 * 2/2013 Raftery .................. G01N 24/08
                                                      702/19

OTHER PUBLICATIONS

Bingol, Kerem et al., Quantitative Analysis of Metabolic Mixtures by Two-Dimensional 13C Constant-Time TOCSY NMR Spectroscopy, Anal. Chem. 2013, 85, 6414-6420.

* cited by examiner

*Primary Examiner* — Edward Raymond
(74) *Attorney, Agent, or Firm* — Sutherland Asbill & Brennan LLP

(57) ABSTRACT

This disclosure provides for new methods for quantification of metabolite concentrations in metabolomics studies, which addresses the difficulties in quantification through 1D peak integrals due to significant peak overlaps in metabolomics samples. For samples from uniformly $^{13}$C-labeled organisms the 2D NMR $^{13}$C-$^{13}$C constant-time (CT) TOCSY experiment provides high-resolution information about individual metabolites that allows their identification via database searching or, in the case of novel compounds, through the reconstruction of their backbone-carbon topology. This disclosure further demonstrates using CT-TOCSY spectra for quantification purposes.

6 Claims, 8 Drawing Sheets

METHODS FOR QUANTITATIVE ANALYSIS OF METABOLIC MIXTURES BY 2D $^{13}$C-CONSTANT-TIME TOCSY NMR SPECTROSCOPY

CROSS REFERENCE TO RELATED APPLICATIONS

This application claims the benefit of U.S. Provisional Application No. 61/823,560, filed May 15, 2013, the disclosure of which is incorporated herein by reference in its entirety.

STATEMENT OF GOVERNMENT INTERESTS

This invention was made with government support under Grant Award No. R01 GM 066041, awarded by the National Institutes of Health. The Government has certain rights in the invention.

FIELD OF THE DISCLOSURE

This disclosure relates to Nuclear Magnetic Spectroscopy (NMR) techniques for quantitative analysis of complex mixtures of compounds.

BACKGROUND

Due to its versatility and quantitative nature, nuclear magnetic resonance (NMR) spectroscopy is one of the most commonly used tools in analytical chemistry.[1,2] 1D $^1$H NMR experiments are widely applied for the extraction of quantitative concentrations of individual chemical species in solution provided that the spectra are well-resolved. A major advantage of 1D $^1$H spectra is that the integral of a given peak is directly proportional to the concentration of the compound it belongs to.[3] 1D $^{13}$C{$^1$H} NMR spectroscopy at natural $^{13}$C abundance can also be used for quantification by targeted profiling using database information.[4]

In the presence of strong peak overlaps, which are typical for complex mixtures such as ones encountered in metabolomics, 1D $^1$H NMR experiments become less useful, and spectra are difficult to analyze. Significant peak overlaps in 1D NMR spectra of metabolomics samples prevents straightforward quantification through 1D peak integrals. While the resolution issue can often be addressed by 2D NMR spectroscopy, the quantification of 2D spectra is hindered by the variability of cross-peak intensities due to uneven magnetization transfer during the preparation, evolution, or mixing periods because of differences in scalar J-couplings and spin relaxation.[5] This feature prevents the direct use of cross-peak integrals as quantitative measures of sample concentrations.

Therefore, what is needed are better methods, including improved NMR methods, that allow the analysis of complex mixtures that are found in metabolomics. In particular, better NMR techniques for the quantitative analysis of mixtures of compounds are needed, such as approaches that might aim to translate cross-peak integrals into concentrations.

SUMMARY

Throughout this disclosure, literature references are presented that are helpful in understanding and illustrating certain aspects of the disclosure. These literature references are cited at various passages of the specification in the manner commonly used for scientific and engineering publications or other disclosures.

In an aspect, this disclosure provides for new methods for quantification of metabolite concentrations in metabolomics studies, which is a key task in metabolomics studies. Significant peak overlaps in 1D NMR spectra of metabolomics samples prevents straightforward quantification through 1D peak integrals. For samples from uniformly $^{13}$C-labeled organisms the 2D NMR $^{13}$C-$^{13}$C constant-time (CT) TOCSY (Total Correlation Spectroscopy) experiments provide high-resolution information about individual metabolites that allows their identification via database searching or, in the case of novel compounds, through the reconstruction of their backbone-carbon topology. It is demonstrated in this disclosure how CT-TOCSY spectra can also be utilized for quantification purposes. This is accomplished through the quantum-mechanical treatment of the TOCSY magnetization transfer or by the use of analytical approximations, which are based on the knowledge of the carbon-backbone topologies. The methods are demonstrated for carbohydrate and amino-acid mixtures, but are applicable across a wide range of systems.

2D NMR quantification methods can be divided into two main groups based on their strategies to deal with the variability of cross-peak intensities mentioned above. The first category uses an internal standard for each type of molecule. This approach has been demonstrated for the heteronuclear 2D $^{13}$C-$^1$H HSQC[6,7] (Heteronuclear Single Quantum Coherence) and the homonuclear 2D $^1$H-$^1$H TOCSY[8] and 2D $^1$H-INADEQUATE experiments.[9] It is rather labor-intensive as it requires the preparation and measurement of a large number of standards. Furthermore, molecules identified in a sample cannot be quantified if their standard is unknown, which includes newly discovered molecules. The second approach aims at minimizing the variability in cross-peak intensities by modification of $^{13}$C-$^1$H HSQC experiments,[10-13] in some cases by extrapolation of a series of experiments.[12] It has the advantage that it does not require an internal standard for each molecule.

The 2D NMR quantification techniques mentioned so far are for metabolite samples at natural $^{13}$C abundance. Uniform $^{13}$C-enrichment of organisms, which is possible for an increasing number of organisms, such as bacteria, yeast, C. elegans, and plants, leads to fully $^{13}$C-labeled metabolites. It has recently been demonstrated that homonuclear $^{13}$C-NMR of complex mixtures of such metabolites offers unique information about their identity and composition. Based on 2D $^{13}$C-$^{13}$C constant-time (CT) TOCSY NMR spectra, the determination of the carbon-backbone topologies of 112 metabolites in a single sample of uniformly $^{13}$C-labeled E. coli could be achieved.[14] In order to optimally utilize the chemical and biological information of such samples, the quantification of individual mixture components is helpful. Here, we present general strategies for the quantification of uniformly $^{13}$C labeled metabolites, which do not require an internal standard for each metabolite. The proposed strategies are either based on the exact quantum-mechanical simulation of 2D CT-TOCSY NMR spectra or on analytical approximations of the exact simulations.[15-17]

Therefore according to one aspect, this disclosure provides for comparing computed or estimated CT-TOCSY peak volumes for each individual compound of interest with the corresponding experimental volumes to identify and determine the relative concentrations of the different compounds. For example, this disclosure provides a spectroscopic method for identifying individual compounds in a chemical mixture, the method comprising:

providing a chemical mixture comprising uniformly $^{13}$C-labeled individual compounds;

obtaining an experimental 2D $^{13}$C-$^{13}$C constant-time (CT) TOCSY NMR spectrum of the chemical mixture using a mixing-time ($\tau_m$) to achieve magnetization transfer and obtain experimental cross-peak volumes;

calculating or estimating cross-peak volumes of 2D $^{13}$C-$^{13}$C constant-time (CT) TOCSY NMR spectra of each individual compound to be quantified in a chemical mixture;

plotting the experimental cross-peak volumes versus the calculated or estimated cross-peak volumes to obtain a cross-peak integral plot of each individual compound; and identifying and/or quantifying individual compounds based on or based solely on spin topology networks derived from cross-peak patterns and the dependence of their volumes on the TOCSY mixing time.

Thus for samples from uniformly $^{13}$C-labeled organisms, the 2D NMR $^{13}$C-$^{13}$C constant-time (CT) TOCSY (Total Correlation Spectroscopy) experiments provide high-resolution information about individual metabolites that allows their identification via database searching or, in the case of novel compounds, through the reconstruction of their backbone-carbon topology. Another aspect provides for further quantifying of the relative concentrations of the individual compounds in the chemical mixture using this method, from the slopes (a) of the experimental and computed peak integral correlation lines.

In this method, the mixing-time $\tau_m$ can be sufficiently long to achieve magnetization transfer across the entire $^{13}$C spin system, or alternatively $\tau_m$ can be sufficiently short to achieve magnetization transfer only between directly connected carbons. In either case, the relative concentration data can then be obtained by comparing the volumes of the non-overlapping experimental cross-peaks with the calculated cross-peak volumes according to this disclosure. According to another aspect, the mixing-time $\tau_m$ can be sufficiently short to achieve magnetization transfer only between directly connected carbons, and relative concentration data can then obtained by comparing the experimental cross peak volumes with the estimating cross-peak volumes from approximations of the TOCSY transfer amplitudes on the basis of the spin system of the individual compound according to this disclosure. These and other aspects and embodiments are described in detail herein.

DETAILED DESCRIPTION

Computational Approaches for Quantification of 2D $^{13}$C-$^{13}$C CT-TOCSY Quantum-Mechanical Description of Cross-Peak Volumes.

Figure 5:
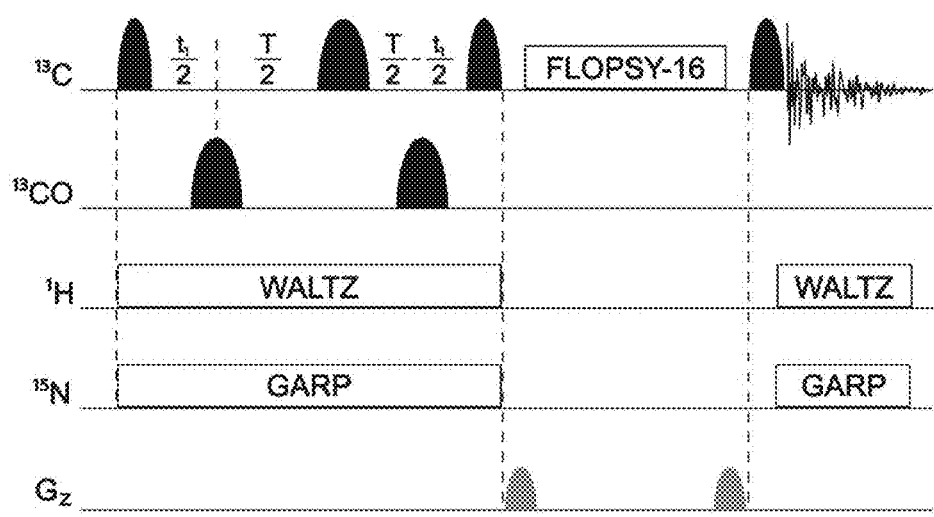
FIG. 5. Pulse sequence of 2D $^{13}$C-$^{13}$C constant-time (CT) TOCSY experiment. Narrow and wide black semi-elliptical shapes on the carbon channel ($^{13}$C) represent π/2 and π shaped radio-frequency pulses, respectively. The constant-time period T is chosen so that T=1/$^1$J$_{CC}$≈1/37.6 Hz=26.6 ms. Pulse phases are cycled as follows: three π/2 pulses from left to right=(x, -x), (x, x, x, x, -x, -x, -x, -x), (x, x, -x, -x); all three it pulses=(x); and receiver phase=(x, -x, -x, x, -x, x, x, -x). The pulse lengths are 248 μs for π/2 pulses and 192 μs for π pulses. The π/2 pulses are Gaussian cascade 4 (G4) pulses (See Emsley, L.; Bodenhausen, G. Chem. Phys. Lett. 1990, 165, 469-476) and the it pulses are Quaternion cascade 3 (Q3) pulses (See Emsley, L.; Bodenhausen, G. J. Magn. Reson. 1992, 97, 135-148). The pulsed-field gradient pulses have a duration of 1 ms with a gradient strength of 38.5 G/cm and 33.7 G/cm, respectively. Quadrature detection in the indirect dimension is achieved by the States-TPPI method. $^1$H and $^{15}$N (in the case of $^{15}$N enriched samples) are decoupled during $t_1$ and $t_2$ periods by WALTZ and GARP schemes, respectively. TOCSY mixing is performed by FLOPSY-16. The mixing times are set to 4.7 ms for short and 47 ms for long TOCSY mixing.

The NMR pulse sequence of the 2D $^{13}$C-$^{13}$C CT-TOCSY experiment[18] is shown in FIG. 5. Constant-time evolution during $t_1$ removes the dominant homonuclear $^1J(^{13}C,^{13}C)$ couplings along the indirect dimension $\omega_1$. The 2D time-domain signal is given by $$s(t_1, t_2) = A \sum_{i,j} c_i \cdot 2^{2-N} \prod_k \cos(\pi^1 J_{ik} T) e^{-T/T_{2i}} \quad (1)$$

$$\cos(\Omega_i t_1) Tr\{e^{-iH_{iso}\tau_m} S_{iz} e^{iH_{iso}\tau_m} S_{jz}\} e^{-T/T_{2j}} e^{i\Omega_j t_2}$$

where A is a spectrometer-dependent prefactor, $c_i$ is the concentration of the metabolite that contains $^{13}$C spin $S_i$, T is the duration of the constant-time interval, $^1J_{ik}$ denotes the $^1J(^{13}C,^{13}C)$ coupling of spin $S_i$ to its directly bonded neighbor $^{13}$C spin $S_k$, $T_{2i}$ is the $T_2$ relaxation time of spin $S_i$ and $\Omega_i$ is its Larmor frequency. N denotes the number of spins $S_i$ and $2^{2-N}$ is a normalization factor. $S_{iz}$ denotes the spin angular momentum product operator along z of spin i, "Tr" denotes the matrix trace and $H_{iso}$ the isotropic mixing Hamiltonian during TOCSY mixing:[19]

$$H_{iso} = \sum_{i<j} 2\pi J_{ij} \{S_{ix}S_{jx} + S_{iy}S_{jy} + S_{iz}S_{jz}\} \quad (2)$$

2D Fourier transformation of $s(t_1,t_2)$ of Eq. (1) leads to the 2D NMR spectrum $S(\omega_1,\omega_2)$. Because of the linearity of the Fourier transform, the integral (volume) of the cross-peak between spins $S_i$ and $S_j$ corresponds to $$V_{ij} = Ac_i \cdot 2^{2-N} \prod_k \cos(\pi^1 J_{ik} T) e^{-T/T_{2i}} Tr\{e^{-iH_{iso}\tau_m} S_{iz} e^{iH_{iso}\tau_m} S_{jz}\} \quad (3)$$

It follows that the concentration $c_i$ of the metabolite that contains the two spins can be estimated according to $c_i = V_{ij}/Af_{ij}$ where the transfer function $$f_{ij}(T, \tau_m) = \quad (4)$$

$$\frac{V_{ij}}{Ac_i} = 2^{2-N} \prod_k \cos(\pi^1 J_{ik} T) e^{-T/T_{2i}} Tr\{e^{-iH_{iso}\tau_m} S_{iz} e^{iH_{iso}\tau_m} S_{jz}\}$$

and the universal prefactor A can be empirically determined as described below. The transfer function of Eq. (4) can be computed because all parameters are either known or can be estimated with good accuracy. Specifically, because in $^{13}$C spin systems the $^1J(^{13}C,^{13}C)$ couplings, which range between 30-55 Hz, dominate the geminal $^2J(^{13}C,^{13}C)$ and vicinal $^3J(^{13}C,^{13}C)$ couplings, knowledge of the backbone topology of a metabolite permits the straightforward determination of $H_{iso}$ (Eq. (2)). Furthermore, since for metabolites the transverse relaxation times $T_2$ by far exceed the constant-time period T, $e^{-T/T_{2i}}$ is close to 1 for all metabolites so that it can be incorporated in prefactor A. $T_1$ and $T_2$ relaxation effects during the TOCSY mixing time $\tau_m$ can be treated in the same way. The constant-time period T is chosen so that $T=1/^1J_{CC} \approx 1/37.6$ Hz=26.6 ms. Therefore, the product in Eq. (4) is $$\prod_k \cos(\pi^1 J_{ik} T) \cong (-1)^m,$$

where m is the number of directly bonded $^{13}$C to spin $S_i$, which explains the modulation of the absolute sign of diagonal and cross-peaks along $\omega_1$ in $^{13}$C-$^{13}$C CT-TOCSY experiments as a function of carbon branching, i.e. primary vs. secondary vs. tertiary vs. quarternary carbon.

Strategies for the Determination of Metabolite Concentrations from 2D $^{13}$C-$^{13}$C CT-TOCSY.

Eqs. (1)-(4) can be directly used for the quantitative prediction of cross-peak and diagonal-peak volumes. The TOCSY transfers, which are dominated by the $^1J(^{13}C,^{13}C)$ couplings, are relatively insensitive to their precise values. By comparing the computed CT-TOCSY peak volumes with the corresponding experimental volumes the relative concentrations of the different compounds can be determined. This approach is demonstrated in 3 different variants, which in the following will be referred to as Methods A, B, C (see also Results and Discussion):

Method A uses a CT-TOCSY spectrum with a relatively long mixing time, e.g. $\tau_m$=47 ms, which ensures magnetization transfer across the whole $^{13}$C spin system. This spectrum displays a maximum number of cross-peaks. Those peaks that are not affected by overlap can be used for quantification by comparing the experimental peak volumes with the ones computed based on Eq. (1).

Method B uses a CT-TOCSY spectrum with a relatively short-mixing time, e.g. $\tau_m$=4.7 ms, where cross-peaks appear only between directly connected carbons. Therefore, this spectrum has fewer cross-peaks than the one of Method A. They can be used for quantification by comparing the experimental peak volumes with the ones computed based on Eq. (1).

Method C uses, like Method B, a CT-TOCSY spectrum with a relatively short-mixing time, e.g. $\tau_m$=4.7 ms. However, the compound quantification is not based on the full quantum-mechanical expression of magnetization transfer. Instead it uses empirically derived approximations given below.

For all three approaches, the topology of each compound of interest is required. This can be achieved by direct compound identification by querying a $^{13}$C TOCSY trace, such as a $^{13}$C consensus TOCSY trace,[20] of the compound of interest taken from a long-mixing CT-TOCSY spectrum against the TOCCATA database.[21] Alternatively, the carbon topology can be reconstructed ab initio based on the analysis of CT-TOCSY spectra measured at long and short TOCSY mixing times.[14] Once the carbon topology is known, the scalar $^1J(^{13}C,^{13}C)$ network ($J_{ij}$ of Eq. (2)) is established by setting $^1J(^{13}C,^{13}C) \approx 35\text{-}40$ Hz, except for $^1J(^{13}C,^{13}C)$ that involve carbonyl or carboxyl carbons, which are set to ~55 Hz. These couplings can also be double-checked from cross-sections of the CT-TOCSY along $\omega_2$. Since all multiple-bond J-couplings are much smaller, they can be safely ignored (i.e. set to zero) for the TOCSY mixing times considered here. For Methods A and B, J-coupling constants $J_{ij}$ are inserted in Eq. (2) to define the isotropic TOCSY Hamiltonian $H_{iso}$ to compute the transfer amplitudes $f_{ij}$ of Eq. (4) at the same mixing time $\tau_m$ used in the experiment. This is accomplished by numerical evaluation of Eq. (4). It is noted that the transfer function $f_{ij}$ of Eq. (4) is normalized, i.e. $f_{ij}(\tau_m=0)=\delta_{ij}(-1)^m$ (where $\delta_{ij}$ is the Kronecker symbol). The average ratio of the experimentally determined peak integrals by the simulated transfers yields the quantity A $c_i$. In addition, the measurement of the peak volume of a component with a known concentration allows the determination of the prefactor A. This can be achieved, for example, by calibration of the spectrum by the addition of a pure compound with known concentration, e.g. 4,4-dimethyl-4-silapentane-1-sulfonic acid (DSS).

Approximate Relationships for Method C.

At short mixing times $\tau_m$ the full numerical integration of Eqs. (1)-(4) can be avoided by using approximate analytical solutions. The following expressions give the TOCSY transfer amplitudes where $s=\sin(\pi^1 J_{CC}\tau_m)$ and $c=\cos(\pi^1 J_{CC}\tau_m)$:

(a) Two-spin system: $S_1$-$S_2$ $$S_{1z} \to c^2 S_{1z} + s^2 S_{2z}, \quad S_{2z} \to c^2 S_{2z} + s^2 S_{1z}$$

(b) Linear three-spin system: $S_1$-$S_2$-$S_3$ $$S_{1z} \to c^2 S_{1z} + s^2 c S_{2z}, \quad S_{2z} \to s^2 c S_{1z} + c^4 S_{2z} + s^2 c S_{3z}, \quad S_{3z} \text{ is analogous to } S_{1z}$$

(c) Linear four-spin system: $S_1$-$S_2$-$S_3$-$S_4$ $$S_{1z} \to c^2 S_{1z} + s^2 c S_{2z}$$
$$S_{2z} \to s^2 c S_{1z} + c^4 S_{2z} + s^2 c^{1.5} S_{3z}$$
$$S_{3z} \text{ is analogous to } S_{2z}$$
$$S_{4z} \text{ is analogous to } S_{1z}$$

(d) Linear five-spin system: $S_1$-$S_2$-$S_3$-$S_4$-$S_5$ $$S_{1z} \to c^2 S_{1z} + s^2 c S_{2z}$$
$$S_{2z} \to s^2 c S_{1z} + c^4 S_{2z} + s^2 c^{1.5} S_{3z}$$
$$S_{3z} \to s^2 c^{1.5} S_{2z} + c^4 S_{3z} + s^2 c^{1.5} S_{4z}$$
$$S_{4z} \text{ is analogous to } S_{2z}$$
$$S_{5z} \text{ is analogous to } S_{1z}$$

Analogous expressions hold for longer linear carbon chains by simply taking into account the number of next and second-next neighbors on each side of the donor spin. For example, for a linear chain $S_1$-$S_2$-$S_3$-$S_4$-$S_5$-$S_6$ the transfers starting from $S_1$ and $S_2$ are the same as for the linear 5-spin system. For symmetry reasons, they also represent the transfers starting from $S_6$ and $S_5$, respectively. The transfers starting from $S_3$ and $S_4$ are identical and they correspond to the one starting from $S_3$ in the linear five-spin system.

(e1) Branched chain (valine-like without —COOH): $S_1$-$S_2$-$S_{3\alpha}$(-$S_{3\beta}$) ($S_2$ is a tertiary carbon)

$$S_{1z} \to c^2 S_{1z} + s^2 S_{2z}$$
$$S_{2z} \to s^2 c^{1.5} S_{1z} + c^6 S_{2z} + s^2 c^{1.5} S_{3\alpha z} + s^2 c^{1.5} S_{3\beta z}$$
$$S_{3\alpha z} \to s^2 c^{1.5} S_{2z} + c^2 S_{3\alpha z}$$
$$S_{3\beta z} \to s^2 c^{1.5} S_{2z} + c^2 S_{3\beta z}$$

(e2) Branched chain (leucine-like without —COOH): $S_1$-$S_2$-$S_3$-$S_{4\alpha}$(-$S_{4\beta}$) ($S_3$ is a tertiary carbon)

$$S_{1z} \to c^2 S_{1z} + s^2 c S_{2z}$$
$$S_{2z} \to s^2 c S_{1z} + c^4 S_{2z} + s^2 c^{2.5} S_{3z}$$
$$S_{3z} \to s^2 c^{2.5} S_{2z} + c^6 S_{3z} + s^2 c^{1.5} S_{4\alpha z} + s^2 c^{1.5} S_{4\beta z}$$
$$S_{4\alpha z} \to s^2 c^{1.5} S_{3z} + c^2 S_{4\alpha z}$$
$$S_{4\beta z} \to s^2 c^{1.5} S_{3z} + c^2 S_{4\beta z}$$

(e3) Branched chain (isoleucine-like without —COOH): $S_1$-$S_2$-($S_{3\beta}$)-$S_{3\alpha}$-$S_4$ ($S_2$ is a tertiary carbon)

$$S_{1z} \to c^2 S_{1z} + s^2 c^{1.5} S_{2z}$$
$$S_{2z} \to s^2 c^{1.5} S_{1z} + c^6 S_{2z} + s^2 c^{2.5} S_{3\alpha z} + s^2 c^{1.5} S_{3\beta z}$$
$$S_{3\alpha z} \to s^2 c^{2.5} S_{2z} + c^4 S_{3\alpha z} + s^2 c S_{4z}$$
$$S_{4z} \to s^2 c S_{3\alpha z} + c^2 S_{4z}$$
$$S_{3\beta z} \to s^2 c^{1.5} S_{2z} + c^2 S_{3\beta z}$$

(f) Star-like topology: $S_1$-$S_{2\alpha}$-$S_{2\beta}$-$S_{2\gamma}$-$S_{2\delta}$ ($S_1$ is the quarternary carbon)

$$S_{1z} \to c^{8.5} S_{1z} + s^2 c^{2.5} S_{2\alpha z} + s^2 c^{2.5} S_{2\beta z} + s^2 c^{2.5} S_{2\gamma z} + s^2 c^{2.5} S_{2\delta z}$$
$$S_{2\alpha z} \to s^2 c^{2.5} S_{1z} + c^{1.5} S_{2\alpha z}$$
$$S_{2\beta z}, S_{2\gamma z}, S_{\delta z} \text{ are analogous to } S_{2\alpha z}$$

To convert the TOCSY transfer amplitudes given by the above expressions into CT-TOCSY peak volumes, they can be multiplied with $\cos(\pi^1 J_{CC}T)^m$ where m is the multiplicity of the donor carbon (which is the carbon whose diagonal peak has the same $\omega_1$ frequency as the cross-peak of interest).

Simulation of Complete 2D $^{13}C$-$^{13}C$ CT-TOCSY Spectra.

This is accomplished by numerical implementation of Eq. (1) using carbon chemical shifts, the carbon-backbone topology, and one-bond $^1J(^{13}C,^{13}C)$ coupling constants of each molecule as input followed by 2D Fourier transformation. For amino acids all $^1J(^{13}C,^{13}C)$ coupling constants were set to 35 Hz, except for coupling to the carboxyl carbons, which are set to 55 Hz. For the carbohydrates $^1J(^{13}C,^{13}C)$ couplings constants are generally larger than 35 Hz[22] and they were set to 40 Hz in the simulations.

NMR Experiments and Processing.

2D $^{13}C$-$^{13}C$ CT-TOCSY[18] data sets of the carbohydrate and amino acid mixtures were collected at 800 MHz proton frequency with 110 ppm $^{13}C$ spectral width at 25° C. with $N_1$=576 and $N_2$=2048 complex data points with 16 scans per increment and a relaxation delay of 4 seconds. TOCSY mixing by FLOPSY-16 of 4.7 ms for short mixing and 47 ms for long mixing were used.[23] 2 D $^{13}$C-$^{13}$C CT-TOCSY data set of galactose was collected at 700 MHz proton frequency with 82 ppm $^{13}$C spectral width at 25° C. with 4.7 ms for short mixing and 37.6 ms for long mixing times using FLOPSY-16.[23] Quantitative 1D $^{13}$C NMR reference spectra were recorded for all samples with a long relaxation delay of 60 seconds. All experimental NMR data sets were zero-filled, Fourier transformed, phase and baseline corrected using NMRPipe[24] and converted to a Matlab-compatible format for subsequent processing and analysis.

Sample Preparation

Amino-Acid Mixture.

A uniformly $^{13}$C labeled amino acid mixture consisting of isoleucine, lysine, alanine and valine with concentrations of 5, 10, 15 and 20 mM, respectively, was prepared in $D_2O$. All amino acids were purchased from Cambridge Isotope Laboratories, Inc.

Carbohydrate Mixture.

The carbohydrate mixture was prepared from uniformly $^{13}$C-labeled glucose (purchased from Sigma-Aldrich) and fructose, galactose, and ribose (purchased from Cambridge Isotope Laboratories, Inc.). A NMR sample was prepared by dissolving these carbohydrates in $D_2O$ each with a 10 mM final concentration. Individual carbohydrate samples were prepared by dissolving each carbohydrate in $D_2O$ with a 10 mM final concentration.

Results and Further Discussion

Figure 1:
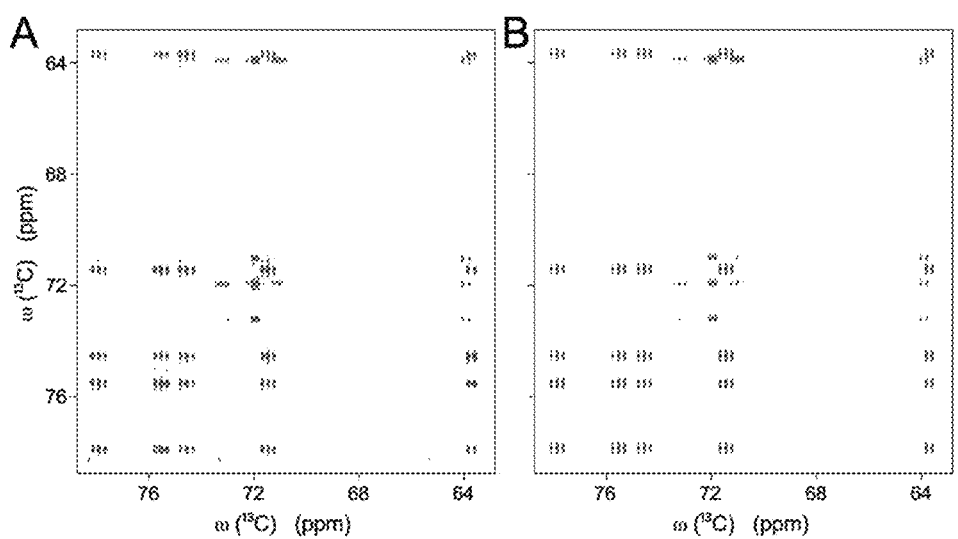
FIG. 1. Side-by-side comparison of (A) experimental and (B) simulated 2D $^{13}$C-$^{13}$C constant-time (CT) TOCSY spectrum of galactose acquired at long TOCSY mixing time. Blue colored peaks are positive and red colored peaks are negative. The simulated spectrum, which uses chemical shifts, backbone topology, and $^1$J(CC) couplings, is based on Eq. (1).

The quantification method of $^{13}$C-$^{13}$C CT-TOCSY spectra is based on the promise that TOCSY transfers can be quantitatively predicted by numerical integration of the Liouville-von Neumann equation that describes the underlying many-spin physics. This is illustrated in FIG. 1 showing a region of the experimental $^{13}$C-$^{13}$C CT-TOCSY spectrum of uniformly $^{13}$C-labeled galactose at a long mixing time (FIG. 1A) in comparison with the computed spectrum (FIG. 1B). In aqueous solution, galactose consists of 2 slowly interconverting isomers, each of which with its distinct resonances. The simulated CT-spectrum of FIG. 1B was computed according to Eq. (1) by the co-addition of the spectra simulated for each of the 2 isomeric states. The high degree of similarity between the simulated and experimental spectra of FIG. 1 exemplifies the potential of CT-TOCSY spectra for quantification of metabolite concentrations.

Quantification of Carbohydrate Mixture.

Figure 2:
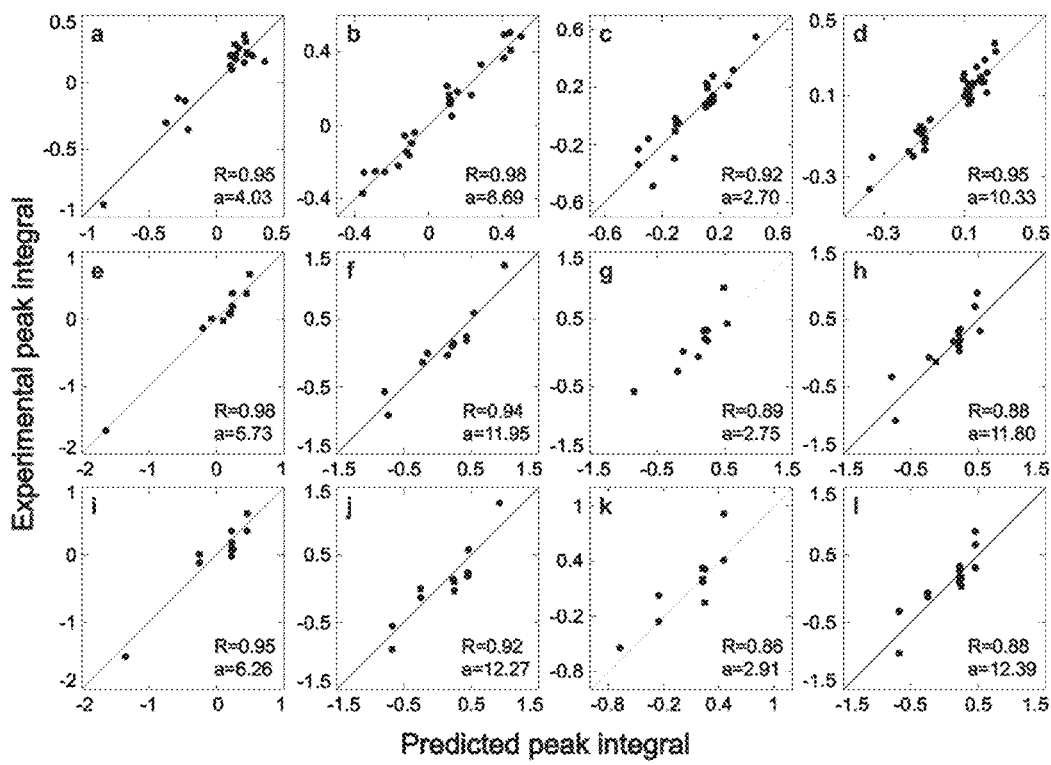
FIG. 2. Quantitative comparison of experimental and simulated cross-peak integrals of 2D $^{13}$C-$^{13}$C constant-time (CT) TOCSY of four different carbohydrates. Panels a, e, i belong to fructose β-furanose, panels b, f, j belong to glucose β-pyranose, panels c, g, k belong to ribose β-furanose, and panels d, h, l belong to galactose β-pyranose. The first row of panels (a, b, c, d) shows the comparison between experimental long mixing-time CT-TOCSY ($\tau_m$=47 ms) and numerical simulation based on Eq. (1) (Method A). The second row of panels (e, f, g, h) shows the comparison between experimental short mixing-time CT-TOCSY ($\tau_m$=4.7 ms) and numerical simulation based on Eq. (1) (Method B). The third row of panels (i, j, k, l) shows the comparison between experimental short mixing-time CT-TOCSY ($\tau_m$=4.7 ms) and numerical results using the analytical approximations (Method C). R and a, which are listed in each panel, stand for correlation coefficient and relative concentration, respectively.
Figure 6:
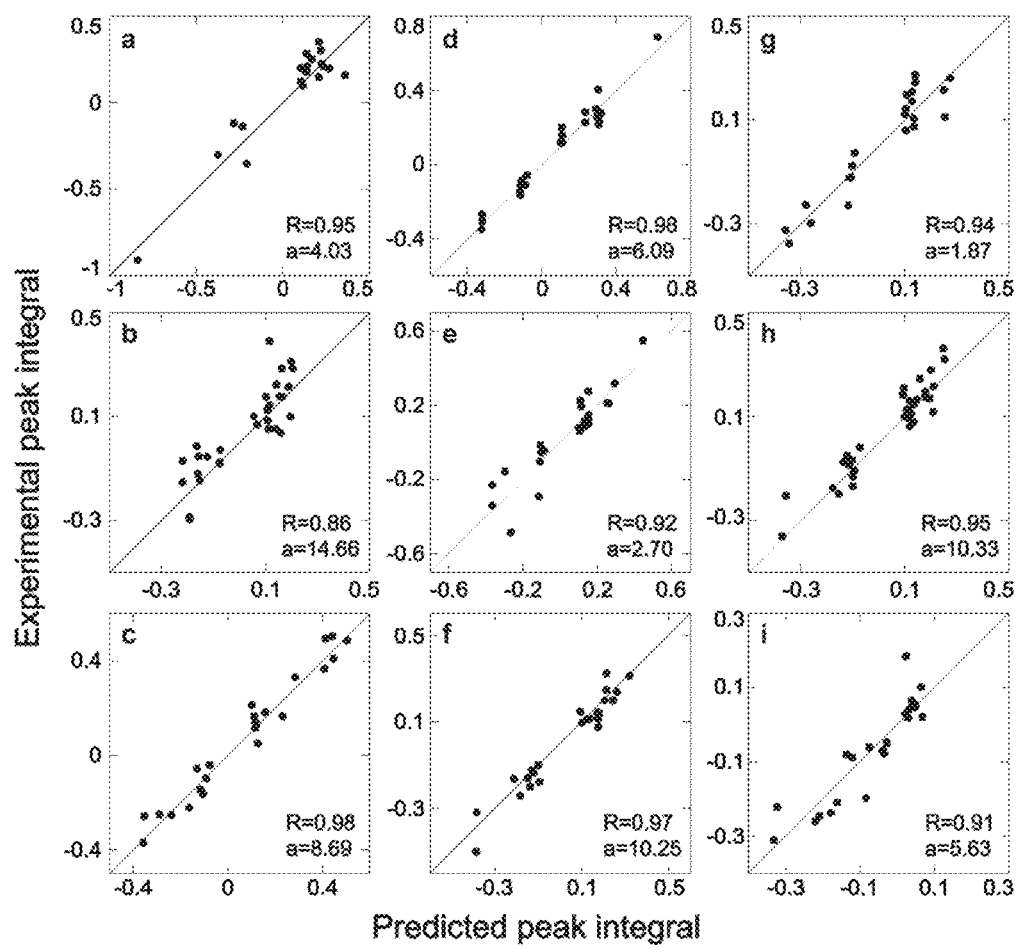
FIG. 6. Quantitative comparison of experimental and simulated (predicted) cross-peak integrals of 2D $^{13}$C-$^{13}$C constant-time (CT) TOCSY with a long mixing time ($\tau_m$=47 ms) of 9 carbohydrate isomers: fructose β-furanose (a), fructose β-pyranose (b), glucose β-pyranose (c), glucose α-pyranose (d), ribose β-furanose (e), ribose β-pyranose (f), ribose α-furanose (g), galactose β-pyranose (h) and galactose α-pyranose (i). Fructose α-furanose is not shown in this figure. The predicted peak integrals are based on the quantum-mechanical treatment of Eq. (1) (Method A). Parameters R and a are defined as in FIGS. 2 and 3.

Our compound quantification method using a long mixing time TOCSY spectrum (Method A) was first tested for a carbohydrate mixture consisting of uniformly $^{13}$C-labeled ribose, glucose, fructose and galactose. In aqueous solution, each of these carbohydrates is present in multiple isomeric forms, which are in slow exchange: 2 isomers in the case of galactose and glucose and three isomers in the case of fructose and ribose. Long mixing time CT-TOCSY simulations were performed for each sugar isomer. In the simulated spectra, the peak integrals of each sugar isomer were measured and plotted against the peak integrals of the experimental mixture spectrum. The results for 4 of the sugar isomers are plotted in FIG. 2 (first row panels a,b,c,d) and the spectra of all sugar isomers are given in FIG. 6. As can be seen from the figure, the experimental and computed peak integrals align well along the diagonal with a correlation coefficient R between 0.92 and 0.98. For the plots, the experimental peak amplitudes were normalized such that the points lie along the main diagonal. The relative concentrations of the various isomers are indicated by the constant α given in each panel, which correspond to the actual slopes. Consistently good results are obtained for all peaks with the exception of peaks whose donor carbon frequency exceeds 100 ppm. This behavior is presumably caused by the larger radio-frequency offset effects and they were excluded from analysis (and are not shown in the figures). Overlapping diagonal peaks were also excluded.

A distinctive feature of long-mixing CT-TOCSY is the large number of cross-peaks as the number of peaks grows with the square of the chain length. For example, for a linear 6-carbon chain, such as α-glucose, the total number of cross-peaks and diagonal peaks is 36. Even in the case of some overlaps, the number of peaks available for quantification of the compound is therefore large. It not only helps reduce the statistical uncertainty, but it also allows identification of 'outliers', which includes peaks whose volumes are affected by spectral artifacts, and thereby increases the confidence and precision of the concentration estimates.

Figure 7:
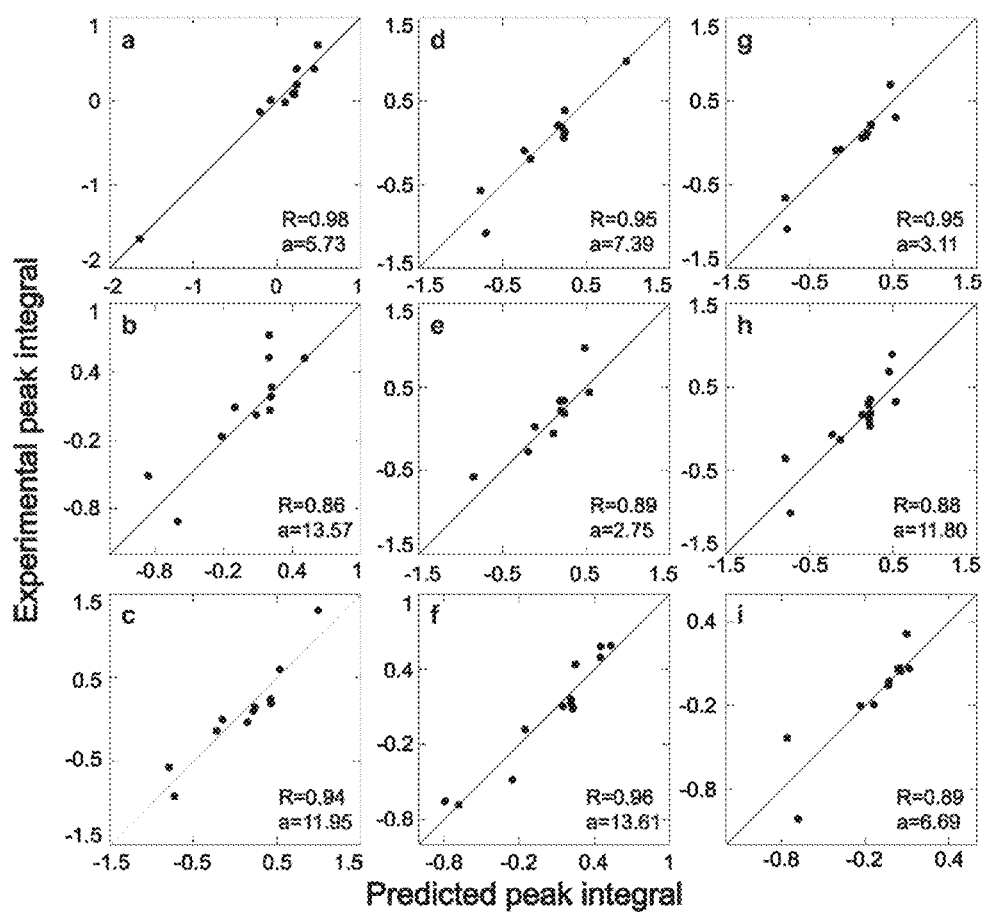
FIG. 7. Quantitative comparison of experimental and simulated (predicted) cross-peak integrals of 2D $^{13}$C-$^{13}$C constant-time (CT) TOCSY with a short mixing time ($\tau_m$=4.7 ms) of the same 9 carbohydrate isomers as in FIG. 6: fructose β-furanose (a), fructose β-pyranose (b), glucose β-pyranose (c), glucose α-pyranose (d), ribose β-furanose (e), ribose β-pyranose (f), ribose α-furanose (g), galactose β-pyranose (h) and galactose α-pyranose (i). The predicted peak integrals are based on the quantum-mechanical treatment of Eq. (1) (Method B). Parameters R and a are defined as in FIGS. 2 and 3.
Figure 8:
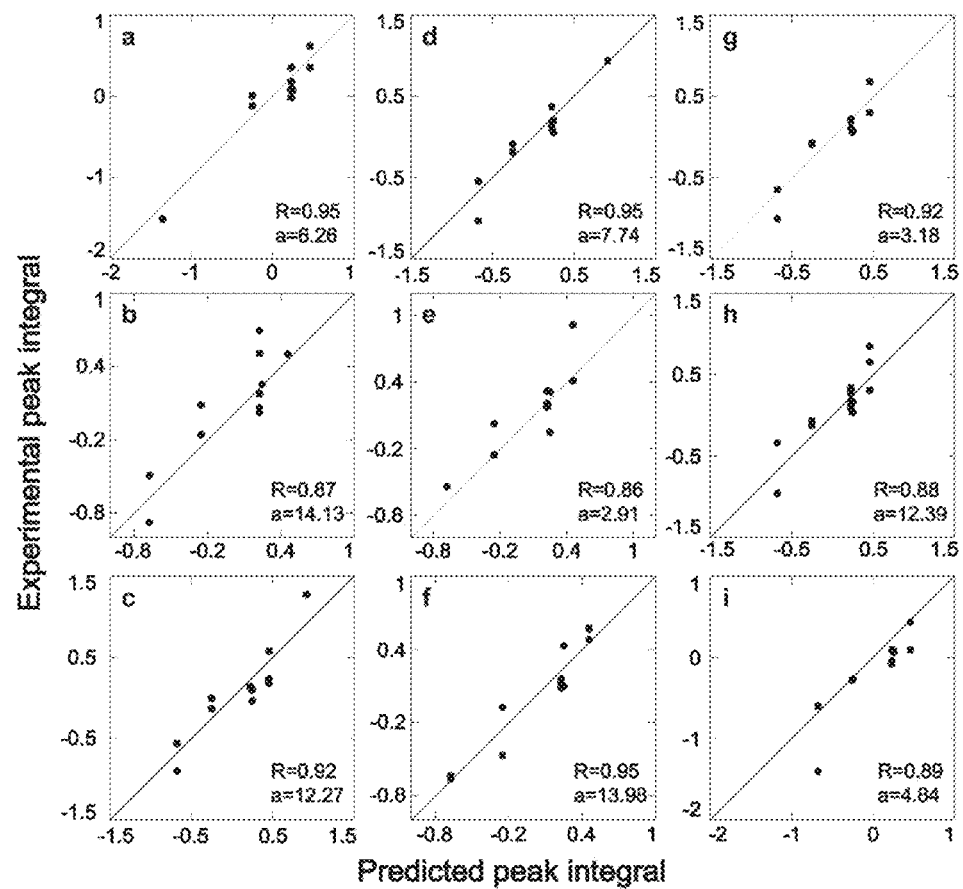
FIG. 8. Quantitative comparison of experimental and simulated (predicted) cross-peak integrals of 2D $^{13}$C-$^{13}$C constant-time (CT) TOCSY with a short mixing time ($\tau_m$=4.7 ms) of the same 9 carbohydrate isomers as in FIG. 6: fructose β-furanose (a), fructose β-pyranose (b), glucose β-pyranose (c), glucose α-pyranose (d), ribose β-furanose (e), ribose β-pyranose (f), ribose α-furanose (g), galactose β-pyranose (h) and galactose α-pyranose (i). The predicted peak integrals are based on the analytical approximations (Method C).

The same procedure used for the analysis of the long-mixing CT-TOCSY spectra was applied to short mixing time CT-TOCSY (Method B). The results for 4 of the carbohydrate isomers are plotted in FIG. 2e,f,g,h and the results for all sugar isomers are shown in FIG. 7. The correlation coefficients between computed and experimental peak volumes vary between 0.88 and 0.98. The short-mixing CT-TOCSY has significantly fewer cross-peaks than the long-mixing TOCSY as the number of peaks grows linearly with the chain length. For example, for a linear 6-carbon chain, such as α-glucose, the total number of peaks is 16.

At long mixing times, analytical solutions do not exist for all but the simplest spin systems. On the other hand, for sufficiently short mixing time, the exact transfer amplitudes can be empirically approximated as shown in the Methods section (Method C). The accuracy of these approximations can be assessed in FIGS. 2i,j,k,l and 8 where the approximate peak volumes at 4.7 ms mixing time are compared with the experimentally extracted volumes at the same mixing time. The correlation coefficients vary between 0.86 and 0.95, which is very similar to the performance of the exact treatment at short mixing times (Method B).

Carbohydrate Isomer Population Determination.

The ability to accurately determine the populations of each isomer of a given carbohydrate is a useful indicator for the accuracy of the different methods. For this purpose, the relative isomer populations determined by 5 different methods are compared in Table 1. Two of these methods are based on a 1D $^{13}$C NMR spectrum of either a sample of a pure compound or the 1D $^{13}$C NMR spectra of the mixture. The other 3 approaches use 2D CT-TOCSY information according to Methods A, B, C. In the case of galactose, Method A yields populations of its two isomers α-pyranose and β-pyranose of 35.3% and 64.7%, respectively. These percentages are close to the ones observed in 1D $^{13}$C NMR spectra of individual galactose (33.3% vs. 66.7%) as well as galactose peaks in 1D $^{13}$C NMR spectra of the carbohydrate mixture (33.2% vs. 66.8%). Methods B and C, which rely on short-mixing CT-TOCSY, yield results with larger deviations (Method B: 36.2% vs. 63.8% and Method C: 28.1% vs. 71.9%). This is primarily due to the smaller number of peaks leading to larger statistical errors and distorted peak shapes caused by the presence of zero-quantum effects. Overall, the 5 methods produce consistent results for both galactose and glucose. For the other 2 carbohydrates, which both have at least one isomer with notably low concentration (<20%), fructose isomer concentrations were determined quite accurately by Method A. Ribose isomer concentrations could be determined less accurately by all three methods, since peaks of the high-population isomer β-pyranose and the low-population isomer α-pyranose overlap throughout the spectrum. Taken together, the long-mixing TOCSY (Method A)

produces somewhat more robust population estimates as judged by their better agreement with the 1D methods than the short-mixing TOCSY.

Quantification of Amino-Acid Mixture.

This sample consists of an aqueous mixture of isoleucine, lysine, alanine and valine with concentrations of 5, 10, 15 and 20 mM, respectively. Long-mixing CT-TOCSY simulations were performed for each amino acid (Method A). From the simulated spectra, peak integrals were extracted and plotted against the corresponding peak integrals of the experimental mixture spectrum (FIG. 3a,b,c,d). Peaks whose donor carbon is a Cα gave relatively large errors and they were excluded from analysis. The correlation coefficients lie between 0.83 (valine) and 0.98 (isoleucine).

The results for the short-mixing TOCSY (Method B) is shown in FIG. 3e,f,g,h with correlation coefficients between 0.99 and 1.00. The relative concentration of isoleucine, lysine and valine can be obtained with reasonably high accuracy. Only for alanine, for which only 2 peaks were used, severe peak distortions leads to a worse performance than for long-mixing CT-TOCSY. The same conclusions hold for the approximate treatment of the short-mixing TOCSY (Method C) with the results shown in FIG. 3i,j,k,l.

Figure 3:
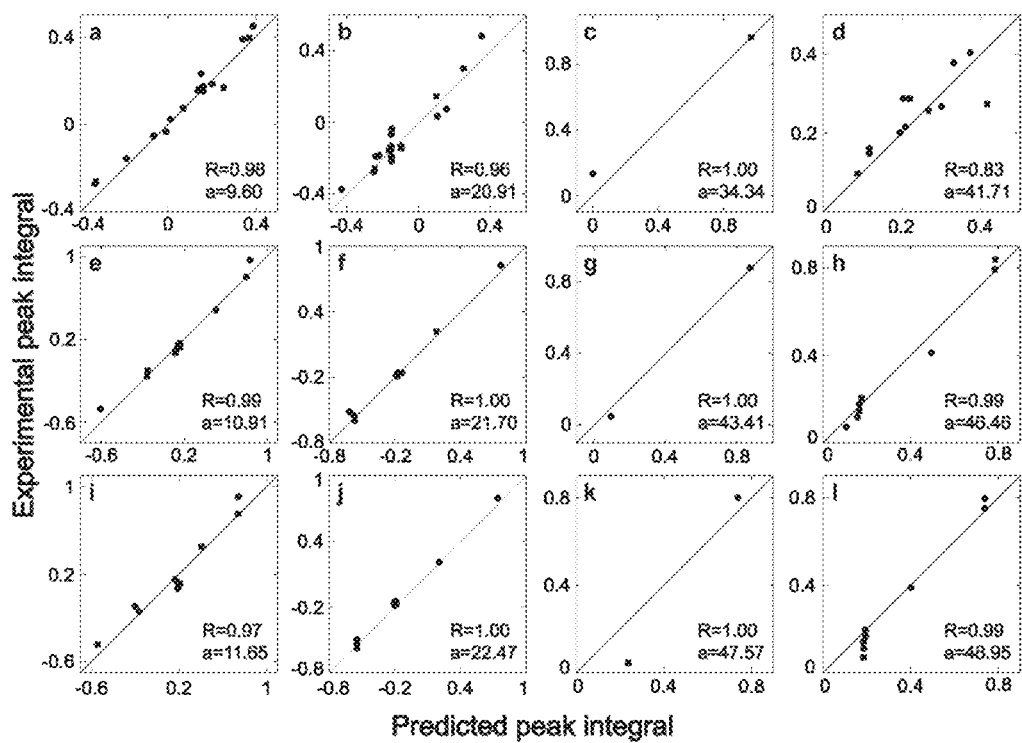
FIG. 3. Quantitative comparison of experimental and simulated cross-peak integrals of 2D $^{13}$C-$^{13}$C constant-time (CT) TOCSY of four different amino acids. Panels a, e, i belong to isoleucine, panels b, f, j belong to lysine, panels c, g, k belong to alanine, and panels d, h, l belong to valine. The first row of panels (a, b, c, d) shows the comparison between experimental long mixing-time CT-TOCSY ($\tau_m$=47 ms) and numerical simulation based on Eq. (1) (Method A). The second row of panels (e, f, g, h) shows the comparison between experimental short mixing-time CT-TOCSY ($\tau_m$=4.7 ms) and numerical simulation based on Eq. (1) (Method B). The third row of panels (i, j, k, l) shows the comparison between experimental short mixing-time CT-TOCSY ($\tau_m$=4.7 ms) and numerical results using the analytical approximations (Method C). R and a, which are listed in each panel, stand for correlation coefficient and relative concentration, respectively.
Figure 4:
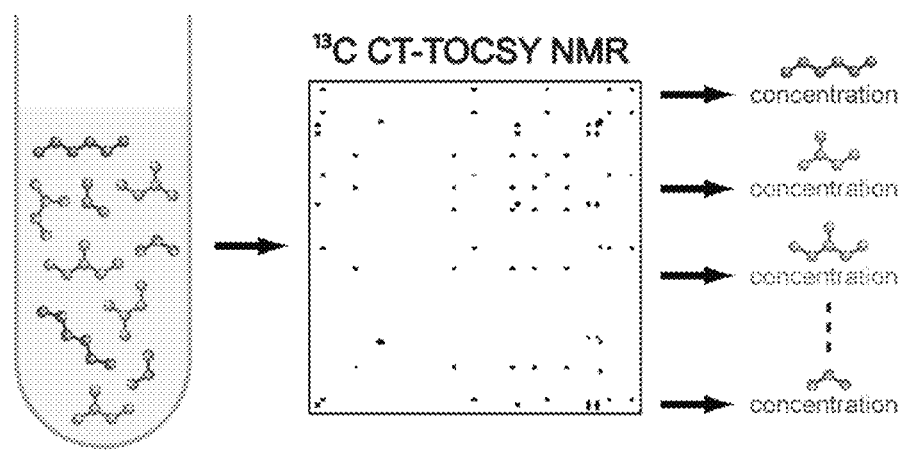
FIG. 4. A general schematic for embodiments of the present disclosure.

The concentration ratios of the amino acids were extracted from FIG. 3 and with the results listed in Table 2. They show that the relative concentrations of isoleucine, lysine and valine can be obtained with high accuracy by all 3 methods. For alanine with only 2 cross-peaks, and hence poorer statistics, the accuracy is clearly lower.

Identification and quantification of metabolites in complex mixtures is a key challenge of metabolomics. Quantification of components by NMR spectroscopy is traditionally based on peak integrals of 1D NMR spectra. This method can provide very accurate concentration estimates, but it is limited to spectra with relatively little peak overlap. For complex metabolite mixtures, such as the ones encountered in metabolomics, peak overlaps in the 1D spectrum are typically prevalent to the extent that they significantly hamper or prevent the use of 1D spectra for quantification. Although the overlap issue can be addressed by taking advantage of the substantial resolution enhancement offered by 2D NMR spectra, magnetization transfers during 2D experiments lead to non-uniform scaling across the spectrum, which impairs the direct proportionality relationship between peak volumes and compound concentration. The course of magnetization transfer in 2D $^{13}$C-$^{13}$C CT-TOCSY experiment is however complex especially at longer mixing times. This experiment is ideally suited for the study of uniformly $^{13}$C-labeled organisms, such as bacteria, yeast, and plants, permitting the ab initio determination of the carbon-backbone topologies of sizeable numbers of known and unknown metabolites.[14] We demonstrate here that this experiment cannot only be used for metabolite identification, but also for quantification purposes provided that the dependence of the cross-peak amplitudes on the mixing time is explicitly taken into account. This can be achieved either through the explicit quantum-mechanical treatment of the underlying spin physics at arbitrary TOCSY mixing times or, in case of short mixing times, by the use of the analytical expressions presented here. Our results for carbohydrates and amino acids show that at long mixing times, the fully quantum-mechanics based calculation of magnetization transfer during TOCSY well reproduces the experimental observations. At shorter mixing times, the accuracy is slightly reduced because of the smaller number of amenable cross-peaks and potentially distorted peak shapes. The achievable accuracy by the 2D CT-TOCSY-based approach is not as high as for the traditional 1D $^1$H NMR approach. However, the use of CT-TOCSY for compound quantification overcomes the need of well-resolved resonances in the 1D NMR spectrum. Application of this quantification method to $^1$H-$^1$H TOCSY spectra is possible, but it requires accurate knowledge of all geminal and vicinal J($^1$H,$^1$H) couplings, which can strongly depend on the metabolite conformation(s). On the other hand, since $^{13}$C CT-TOCSY approach is $^{13}$C-based during both evolution and detection, it does neither require any $^1$H resonance assignments nor knowledge of J($^1$H,$^1$H)-couplings. It can be applied to the very same $^{13}$C-$^{13}$C TOCSY spectra used for compound identification and backbone-carbon topology reconstruction. Moreover, the protocol should be applicable to fractionally $^{13}$C-labeled metabolites, such as ones encountered in flux analysis, provided that cross-peaks of differentially labeled variants of the same molecule do not overlap to an extent that might hinder the accurate measurement of individual cross-peak volumes. These properties make CT-TOCSY spectra a powerful tool for metabolomics studies of $^{13}$C-labeled organisms that aim at compound identification and quantification.

TABLE 1

Quantification results for carbohydrate mixture.

| | A[a] | B[b] | C[c] | 1D Mixture[d] | 1D Individual[e] |
|---|---|---|---|---|---|
| galactose β-pyranose | 64.7% | 63.8% | 71.9% | 66.8% | 66.7% |
| galactose α-pyranose | 35.3% | 36.2% | 28.1% | 33.2% | 33.3% |
| glucose β-pyranose | 58.8% | 61.8% | 61.3% | 63.3% | 62.5% |
| glucose α-pyranose | 41.2% | 38.2% | 38.7% | 36.7% | 37.5% |
| fructose β-furanose | 20.0% | 22.3% | 22.4% | 21.6% | 24.2% |
| fructose β-pyranose | 72.8% | 52.8% | 50.7% | 70.5% | 69.4% |
| fructose α-furanose | 7.2% | 24.9% | 26.9% | 7.9% | 6.4% |
| ribose β-furanose | 18.2% | 14.1% | 14.5% | 13.0% | 12.9% |
| ribose β-pyranose | 69.2% | 69.9% | 69.6% | 80.6% | 80.4% |
| ribose α-furanose | 12.6% | 16.0% | 15.9% | 6.4% | 6.7% |

[a]Results when Method A is used for quantification.
[b]Results when Method B is used for quantification.
[c]Results when Method C is used for quantification.
[d]Quantification from 1D $^{13}$C NMR spectrum of carbohydrate mixture.
[e]Quantification from 1D $^{13}$C NMR spectra of individual carbohydrates.

TABLE 2

Quantification results for amino acid mixture.

| | A[a] | B[b] | C[c] | 1D Mixture[d] | Gravimetric[e] |
|---|---|---|---|---|---|
| Isoleucine | 1.00x | 1.00x | 1.00x | 1.00x | 1.00x |
| Lysine | 2.18x | 1.99x | 1.93x | 2.07x | 2.00x |
| Alanine | 3.58x | 3.98x | 4.08x | 2.94x | 3.00x |
| Valine | 4.34x | 4.26x | 4.20x | 4.10x | 4.00x |

[a]Results when Method A is used for quantification.
[b]Results when Method B is used for quantification.
[c]Results when Method C is used for quantification.
[d]Quantification from 1D $^{13}$C NMR spectrum of amino acid mixture.
[e]Relative amino acid concentrations when amino acid mixture was prepared.

While the methods disclosed herein are demonstrated for carbohydrate and amino-acid mixtures, but are applicable across a wide range of systems. For example, the methods and techniques disclosed here can be applied to biological mixtures generally including metabolic mixtures that include carbohydrates, amino acids, peptides, polypeptides, nucleobases, nucleosides, nucleotides, or any mixtures or combinations thereof.

REFERENCES (1) Lenz, E. M.; Wilson, I. D. *J. Proteome Res.* 2007, 6, 443-458.
(2) Robinette, S. L.; Brüschweiler, R.; Schroeder, F. C.; Edison, A. S. *Acc. Chem. Res.* 2012, 45, 288-297.
(3) Pauli, G. F.; Jaki, B. U.; Lankin, D. C. *J. Nat. Prod.* 2005, 68, 133-149.
(4) Shaykhutdinov, R. A.; MacInnis, G. D.; Dowlatabadi, R.; Weljie, A. M.; Vogel, H. J. *Metabolomics* 2009, 5, 307-317.
(5) Pauli, G. F.; Godecke, T.; Jaki, B. U.; Lankin, D. C. *J. Nat. Prod.* 2012, 75, 834-851.
(6) Lewis, I. A.; Schommer, S. C.; Hodis, B.; Robb, K. A.; Tonelli, M.; Westler, W. M.; Sussman, M. R.; Markley, J. L. *Anal. Chem.* 2007, 79, 9385-9390.
(7) Gronwald, W.; Klein, M. S.; Kaspar, H.; Fagerer, S. R.; Nurnberger, N.; Dettmer, K.; Bertsch, T.; Oefner, P. J. *Anal. Chem.* 2008, 80, 9288-9297.
(8) Gowda, G. A. N.; Tayyari, F.; Ye, T.; Suryani, Y.; Wei, S. W.; Shanaiah, N.; Raftery, D. *Anal. Chem.* 2010, 82, 8983-8990.
(9) Martineau, E.; Tea, I.; Akoka, S.; Giraudeau, P. *NMR Biomed.* 2012, 25, 985-992.
(10) Rai, R. K.; Tripathi, P.; Sinha, N. *Anal. Chem.* 2009, 81, 10232-10238.
(11) Koskela, H.; Heikkila, O.; Kilpelainen, I.; Heikkinen, S. *J. Magn. Reson.* 2010, 202, 24-33.
(12) Hu, K.; Westler, W. M.; Markley, J. L. *J. Am. Chem. Soc.* 2011, 133, 1662-1665.
(13) Rai, R. K.; Sinha, N. *Anal. Chem.* 2012, 84, 10005-10011.
(14) Bingol, K.; Zhang, F.; Bruschweiler-Li, L.; Brüschweiler, R. *J. Am. Chem. Soc.* 2012, 134, 9006-9011.
(15) Cavanagh, J.; Chazin, W. J.; Rance, M. *J. Magn. Reson.* 1990, 87, 110-131.
(16) Brüschweiler, R.; Ernst, R. R. *J. Magn. Reson.* 1997, 124, 122-126.
(17) Butler, M. C.; Dumez, J.-N.; Emsley, L. *Chem. Phys. Lett.* 2009, 477, 377-381.
(18) Eletsky, A.; Moreira, O.; Kovacs, H.; Pervushin, K. *J. Biomol. NMR* 2003, 26, 167-179.
(19) Braunschweiler, L.; Ernst, R. R. *J. Magn. Reson.* 1983, 53, 521-528.
(20) Bingol, K.; Brüschweiler, R. *Anal. Chem.* 2011, 83, 7412-7417.
(21) Bingol, K.; Zhang, F.; Bruschweiler-Li, L.; Brüschweiler, R. *Anal. Chem.* 2012, 84, 9395-9401.
(22) Azurmendi, H. F.; Freedberg, D. I. *J. Magn. Reson.* 2013, 228, 130-135.
(23) Kadkhodaie, M.; Rivas, O.; Tan, M.; Mohebbi, A.; Shaka, A. J. *J. Magn. Reson.* 1991, 91, 437-443.
(24) Delaglio, F.; Grzesiek, S.; Vuister, G. W.; Zhu, G.; Pfeifer, J.; Bax, A. *J. Biomol. NMR* 1995, 6, 277-293.

Each of the references or citations provided in this disclosure is incorporated herein by reference in pertinent part. To the extent that any definition or usage provided by any document incorporated by reference conflicts with the definition or usage provided herein, the definition or usage provided herein controls. In any application before the United States Patent and Trademark Office, the Abstract of this application is provided for the purpose of satisfying the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that are employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

We claim:

1. A spectroscopic method for identifying individual compounds in a metabolic mixture derived from a uniformly $^{13}$C-labeled organism, the method comprising:
    providing a metabolic mixture derived from a uniformly $^{13}$C-labeled organism;
    obtaining an experimental 2D $^{13}$C-$^{13}$C constant-time (CT) TOCSY NMR spectrum of the metabolic mixture using a mixing-time ($\tau_m$) sufficiently short to achieve magnetization transfer only between directly connected carbons and obtain experimental cross-peak volumes;
    estimating cross-peak volumes of 2D $^{13}$C-$^{13}$C constant-time (CT) TOCSY NMR spectra of each individual compound to be quantified in a metabolic mixture from approximations of the TOCSY transfer amplitudes on the basis of the spin system of each compound;
    plotting the experimental cross-peak volumes versus the estimated cross-peak volumes to obtain a cross-peak integral plot of each individual compound; and
    identifying the individual compounds in the metabolic mixture based on spin topology networks derived from the cross-peaks and the dependence of the cross-peak volumes on the TOCSY mixing-time.

2. The spectroscopic method according to claim 1, further comprising quantifying the relative concentrations of the individual compounds in the metabolic mixture from the slopes (a) of the experimental and computed peak integral correlation lines.

3. The spectroscopic method according to claim 1, wherein the step of estimating cross-peak volumes of each individual compound to be quantified comprises multiplying the TOCSY transfer amplitudes by $\cos(\pi^1 J_{CC} T)^m$, wherein m is the multiplicity of the carbon whose diagonal peak has the same $\omega_1$ frequency as the cross-peak of interest.

4. The spectroscopic method according to claim 1, wherein the method is carried out in the absence of an internal standard.

5. The spectroscopic method according to claim 1, wherein the mixture comprises carbohydrates, amino acids, peptides, polypeptides, nucleobases, nucleosides, nucleotides, or combinations thereof.

6. The spectroscopic method according to claim 1, wherein the method provides individual metabolite information of sufficiently high resolution that individual metabolites are identified via database searching or through a reconstruction of their backbone-carbon topology.

* * * * *